US006722367B1

United States Patent
Blom

(10) Patent No.: US 6,722,367 B1
(45) Date of Patent: Apr. 20, 2004

(54) VALVED FENESTRATED TRACHEOTOMY TUBE HAVING OUTER AND INNER CANNULAE

(75) Inventor: Eric D. Blom, Carmel, IN (US)

(73) Assignee: Hansa Medical Products, Inc., Indianapolis, IN (US)

( * ) Notice: Subject to any disclaimer, the term of this patent is extended or adjusted under 35 U.S.C. 154(b) by 0 days.

(21) Appl. No.: 09/576,043

(22) Filed: May 23, 2000

Related U.S. Application Data

(63) Continuation-in-part of application No. 09/398,110, filed on Sep. 16, 1999, now abandoned, which is a continuation-in-part of application No. 09/360,274, filed on Jul. 26, 1999, now abandoned, and a continuation of application No. 08/996,282, filed on Dec. 22, 1997, now Pat. No. 5,957,978.

(51) Int. Cl.[7] .................... A61M 16/00; A61M 25/00
(52) U.S. Cl. ...................... 128/207.14; 128/207.15; 604/264
(58) Field of Search .................. 128/200.24, 200.26, 128/207.14, 207.15, 207.16, 207.17, 207.18, 207.29, 912, 205.24; 623/9; 604/264, 523, 524, 525, 530, 531; 381/70; 600/585

(56) References Cited

U.S. PATENT DOCUMENTS

| 3,688,774 A | | 9/1972 | Akiyama | |
|---|---|---|---|---|
| 3,996,939 A | * | 12/1976 | Sheridan et al. | ....... 128/207.14 |
| 4,211,234 A | | 7/1980 | Fisher | |

(List continued on next page.)

FOREIGN PATENT DOCUMENTS

| DE | 25 05 123 | 1/1976 |
|---|---|---|
| DE | 37 20 482 A1 | 12/1988 |
| DE | 38 13705 A1 | 1/1989 |
| DE | 195 13 831 | 5/1996 |
| WO | 99/07428 | 2/1999 |
| WO | 99/12599 | 3/1999 |
| WO | 00/32262 | 6/2000 |

OTHER PUBLICATIONS

Quick Reference Guide to Shiley's "Quality–Of Life" Line of Tracheostomy Products, 1991.
Granuloma Associated with Fenestrated Tracheostomy Tubes, padmanabhan Siddharth, MD, PhD, FACS and Lawrence Mazzarella, MD, FACS, Case Reports, vol. 150, Aug. 1985, pp. 279–280.

(List continued on next page.)

Primary Examiner—Aaron J. Lewis
Assistant Examiner—Teena Mitchell
(74) Attorney, Agent, or Firm—Barnes & Thornburg

(57) ABSTRACT

An outer cannula has a first port for orienting outside the neck of a wearer, a second port for orienting within the trachea of the wearer, a first passageway coupling the first port to the second port to permit the flow of gases from the first port to the second during inhalation by the wearer and from the second port during exhalation by the wearer, and a third port between the first and second ports. An inner cannula is configured for insertion into the first passageway via the first port when the wearer desires to be able to exhale through his or her pharynx. The inner cannula includes a fourth port for orienting adjacent the first port, a fifth port for orienting adjacent the second port and a second passageway coupling the fourth port to the fifth port to permit the flow of gases from the fourth port to the fifth during inhalation by the wearer and from the fifth port during exhalation by the wearer. A valve controls flow through the third port. The valve assumes a first orientation to permit flow from the first port to the second port when the first port is at a higher pressure than the second port, and a second orientation to permit flow from the second port through the third port when the second port is at a higher pressure than the first port.

23 Claims, 8 Drawing Sheets

U.S. PATENT DOCUMENTS

| | | | | |
|---|---|---|---|---|
| 4,223,411 | A | 9/1980 | Schoendorfer et al. | |
| 4,280,492 | A | 7/1981 | Latham | |
| 4,304,228 | A | 12/1981 | Depel | |
| 4,449,523 | A | 5/1984 | Szachowicz | |
| 4,459,984 | A | 7/1984 | Liegner | |
| 4,573,460 | A | 3/1986 | Szachowicz | |
| 4,589,410 | A * | 5/1986 | Miller | 128/207.15 |
| 4,596,248 | A | 6/1986 | Lieberman | |
| 4,852,565 | A | 8/1989 | Eisele | |
| 5,056,515 | A | 10/1991 | Abel | |
| 5,107,828 | A * | 4/1992 | Koss et al. | 128/200.26 |
| 5,217,008 | A | 6/1993 | Lindholm | |
| 5,255,676 | A | 10/1993 | Russo | |
| 5,297,546 | A * | 3/1994 | Spofford et al. | 128/207.14 |
| 5,329,921 | A | 7/1994 | Socaris | |
| 5,339,808 | A | 8/1994 | Don Michael | |
| 5,343,857 | A | 9/1994 | Schneider et al. | |
| 5,349,950 | A | 9/1994 | Ulrich et al. | |
| 5,391,205 | A | 2/1995 | Knight | |
| 5,392,775 | A | 2/1995 | Adkins, Jr. et al. | |
| 5,458,139 | A | 10/1995 | Pearl | |
| 5,497,768 | A | 3/1996 | Lomholt | |
| 5,507,279 | A * | 4/1996 | Fortune et al. | 128/200.26 |
| 5,515,844 | A | 5/1996 | Christopher | |
| 5,584,288 | A | 12/1996 | Baldwin | |
| 5,599,333 | A | 2/1997 | Atkinson | |
| RE35,595 | E * | 8/1997 | Six | 128/200.26 |
| 5,687,767 | A | 11/1997 | Bowers | |
| 5,688,256 | A | 11/1997 | Surratt et al. | |
| 5,746,199 | A | 5/1998 | Bayron et al. | |
| 5,771,888 | A * | 6/1998 | Keim | 128/207.15 |
| 5,957,978 | A | 9/1999 | Blom | |
| 6,053,167 | A | 4/2000 | Waldeck | |
| 6,089,225 | A | 7/2000 | Brown et al. | |
| 6,102,038 | A | 8/2000 | DeVries | |
| 6,105,577 | A | 8/2000 | Varner | |
| 6,135,111 | A * | 10/2000 | Mongeon | 128/207.15 |
| 6,463,927 | B1 * | 10/2002 | Pagan | 128/200.26 |

OTHER PUBLICATIONS

Technical Support Information Connections with the Passy–Muir Tracheostomy and Ventilator Speaking Valves, one sheet.

Tracheostomy and Laryngectomy Tubes, pp. 568 and 572.

Tracheostomy Tube Adult Home Care Guide, Shiley Tracheostomy Products, Mallinckrodt Medical pp. 1–40.

D. Hessler, MD, K. Rehder, MD and S.W. Karveth, MD, "Tracheostomy Cannula for Speaking During Artificial Respiration", Anesthesiology, vol. 25, No. 5, pp. 719–721 (1964).

* cited by examiner

VALVED FENESTRATED TRACHEOTOMY TUBE HAVING OUTER AND INNER CANNULAE

CROSS-REFERENCE TO RELATED APPLICATIONS

This is a continuation-in-part of U.S. Ser. No. 09/398,110 filed Sep. 16, 1999 now abandoned and titled Valved Fenestrated Tracheotomy Tube Having Outer and Inner Cannulae. U.S. Ser. No. 09/398,110 is a continuation-in-part of U.S. Ser. No. 09/360,274 filed Jul. 26, 1999 now abandoned and titled Valved Fenestrated Tracheotomy Tube. U.S. Ser. No. 09/360,274 is a continuation of U.S. Ser. No. 08/996,282 filed Dec. 22, 1997 and titled Valved Fenestrated Tracheotomy Tube, now U. S. Pat. No. 5,957,978. U.S. Ser. No. 09/398,110 and U.S. Ser. No. 09/360,274 are both now abandoned. The disclosures of these prior applications are hereby incorporated herein by reference.

FIELD OF THE INVENTION

This invention relates to improvements in tracheotomy tubes.

BACKGROUND OF THE INVENTION

This invention is directed toward the problem of being unable to produce audible laryngeal voice, and thus, the inability to speak, that confronts individuals whose breathing is provided mechanically by a respirator which is connected to a cuffed tracheotomy tube inserted into the trachea of a wearer below the level of the vocal cords. The cuff on the tracheotomy tube is inflated, for example, with air, so that the cuff seals substantially fluid tight against the wall of the trachea. The purposes of the inflated cuff include: to protect against leakage of saliva and other secretions around the tracheotomy tube and into the lungs; and, to prevent the air being delivered under pressure from the respirator through the tracheotomy tube to the lungs and exhalation from the lungs from escaping around the tracheotomy tube and out through the mouth and nose of the wearer. In other words, the inflated cuff provides a closed mechanical respiratory system that completely bypasses the upper airway above the level of the tracheotomy tube, including the vocal cords. The side effects of this include the elimination of exhaled airflow upward through the vocal cords. Of course, this eliminates voice production and audible speech.

Currently, there are only two available options for individuals being mechanically ventilated via a cuffed tracheotomy tube to produce audible voice and speech with their own vocal cords. The first of these options is described in O. Hessler, M. D., K. Rehder, M. D., and S. W. Karveth, MC, U. S. A., "Tracheostomy Cannula for Speaking During Artificial Respiration," Anesthesiology, vol. 25, no. 5, pp.719–721 (1964). There is no known commercially available device constructed as described in Hessler, et al.

The second option is a so-called "talking tracheotomy tube," which is a conventional cuffed tracheotomy tube manufactured with an 8–10 French conduit extending along its length. The distal end of this conduit terminates above the level of the inflated cuff. The proximal end of this conduit is connected to a source of, for example, compressed air. Examples of such a device are manufactured by Sims Portex, Inc., and Bivona Surgical Inc. The wearer of such a device is able to stop and start the flow of compressed air to the distal end of this conduit, thereby enabling the stopping and starting of the flow of air upward through his or her vocal cords, enabling the wearer to produce speech. This speech airflow is completely independent of the respiratory airflow through the tracheotomy tube. Such talking tracheotomy tubes have been available for several years, but are not in widespread use, perhaps owing to numerous mechanical limitations.

A ventilator-dependent patient breathing through cuffed tracheotomy tube is unable to produce audible voice with his or her vocal cords because the cuff of the tracheotomy tube he or she wears prevents exhalations from going around the lower end of the tube and upward through the vocal cords. This situation continues until the wearer's condition improves sufficiently that the cuff on the tracheotomy tube can be deflated so that exhaled air can pass around the tracheotomy tube and up through the wearer's vocal cords, mouth and nose, permitting audible vocal cord vibrations for speech.

The invention alleviates this situation. When coupled to a respirator with its cuff inflated, a valved, cuffed tracheotomy tube system according to the invention directs air on the inhalation cycle of the respirator to the lungs. Exhalations are directed by the valved, cuffed tracheotomy tube system according to the invention to the upper airway, permitting vocal cord vibration and audible laryngeal speech.

DISCLOSURE OF THE INVENTION

According to one aspect of the invention, an outer cannula has a first port for orienting outside the neck of a wearer, a second port for orienting within the trachea of the wearer, a first passageway coupling the first port to the second port to permit the flow of gases from the first port to the second during inhalation by the wearer and from the second port during exhalation by the wearer, and a third port between the first and second ports. An inner cannula is configured for insertion into the first passageway via the first port when the wearer desires to be able to exhale through his or her pharynx. The inner cannula includes a fourth port for orienting adjacent the first port, a fifth port for orienting adjacent the second port and a second passageway coupling the fourth port to the fifth port to permit the flow of gases from the fourth port to the fifth during inhalation by the wearer and from the fifth port during exhalation by the wearer. A valve controls flow through the third port. The valve assumes a first orientation to permit flow from the first port to the second port when the first port is at a higher pressure than the second port, and a second orientation to permit flow from the second port through the third port when the second port is at a higher pressure than the first port.

Illustratively according to the invention, the valve includes a movable member and a seat. The movable member moves away from the seat to permit flow from the fourth port to the fifth port when the fourth port is at a higher pressure than the fifth port, and seats against the seat to impede flow from the fifth port through the fourth port and promote flow from the fifth port through the third port when the fourth port is at a lower pressure than the fifth port.

Illustratively according to the invention, the seat is provided in the second passageway.

Alternatively illustratively according to the invention, the seat is provided in the first passageway.

Additionally according to the invention, the valve includes a movable member and a seat. The movable member moves toward the seat to impede flow from the fourth port through the third port when the fourth port is at a higher pressure than the fifth port, and moves away from the seat to permit flow from the fifth port through the third port when the fourth port is at a lower pressure than the fifth port.

Further illustratively according to the invention, the outer cannula includes an inflatable cuff between the second and third ports and a third passageway for introducing an inflating fluid into the cuff in situ in the trachea of the wearer to impede the flow of fluids between the cuff and the trachea when the cuff is inflated.

Additionally illustratively according to the invention, the outer cannula includes a flexible member for covering the third port.

Illustratively according to the invention, the flexible member and the outer cannula include complementary first and second attachment members, respectively, for attaching the flexible member to the outer cannula. The second attachment member provides an attachment point located within the third port for attachment of the first attachment member to the second attachment member at the attachment point.

Alternatively illustratively according to the invention, the flexible member comprises a flexible membrane having a slit in it.

Alternatively illustratively according to the invention, the flexible member comprises a flap for covering the third.

According to another aspect of the invention, a tracheotomy cannula has a first port for orienting outside the neck of a wearer, a second port for orienting within the trachea of the wearer and a first passageway coupling the first port to the second port to permit the flow of gases from the first port to the second during inhalation by the wearer and from the second port during exhalation by the wearer. The cannula includes a portion formed from a thermoplastic material having a first, generally curved orientation when said portion is maintained substantially below body temperature and a second, somewhat inverted L-shaped configuration when said portion is warmed substantially to body temperature.

According to another aspect of the invention, a tracheotomy cannula has a first port for orienting outside the neck of a wearer, a second port for orienting within the trachea of the wearer and a first passageway between the first port and the second port to permit the flow of gases from the first port to the second during inhalation by the wearer and from the second port during exhalation by the wearer. The cannula includes a portion formed from a relatively more flexible material. A stylet is formed from a relatively less flexible material. The stylet has a generally curved orientation. The tracheotomy cannula has a somewhat inverted L-shaped configuration when the stylet is not inserted into the first passageway and a generally curved orientation when the stylet is inserted into the first passageway.

BRIEF DESCRIPTION OF THE DRAWINGS

The invention may best be understood by referring to the following detailed description and accompanying drawings which illustrate the invention. In the drawings.

DETAILED DESCRIPTIONS OF ILLUSTRATIVE EMBODIMENTS

Figure 1:
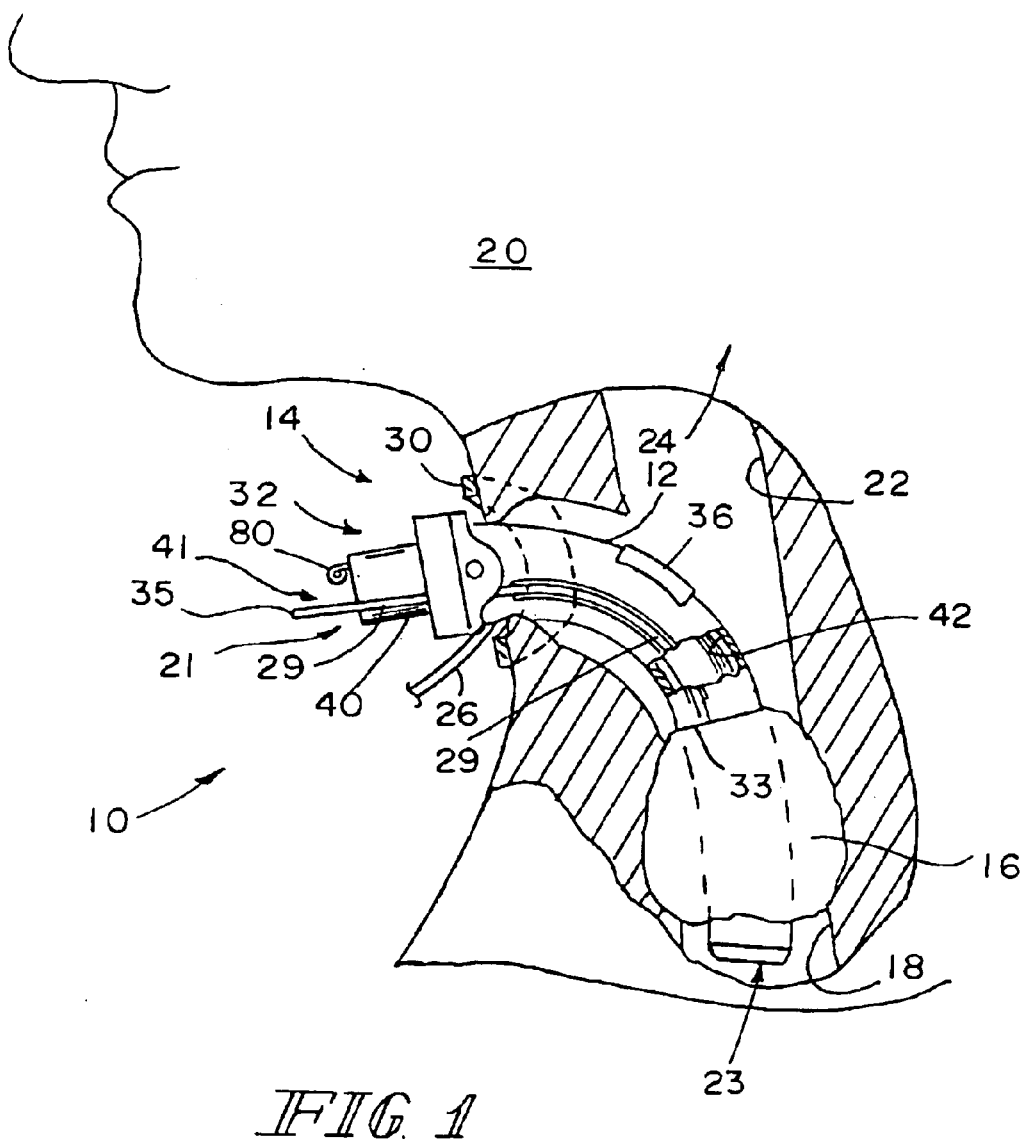
FIG. 1 illustrates a partly fragmentary lateral section through the trachea, tracheostoma and lower pharynx of a wearer fitted with a device according to the present invention.
Figure 2:
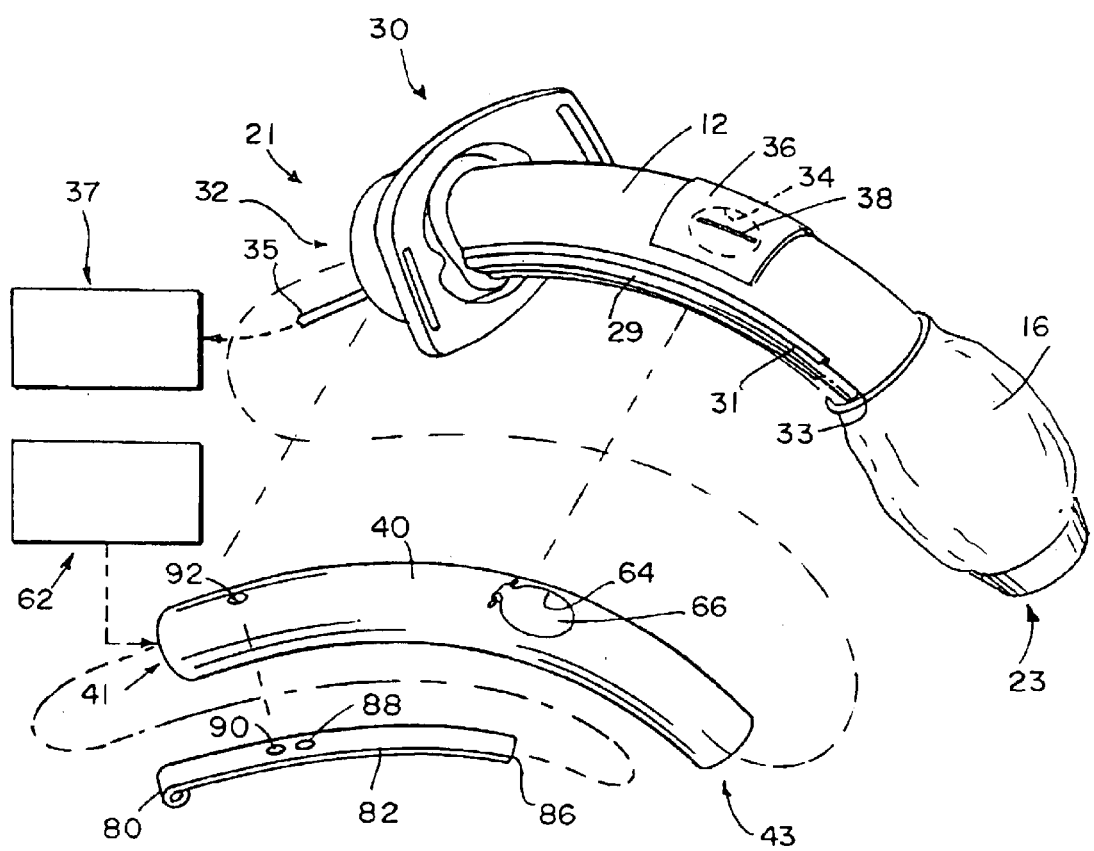
FIG. 2 illustrates an exploded perspective view of the device illustrated in FIG. 1.
Figure 3:
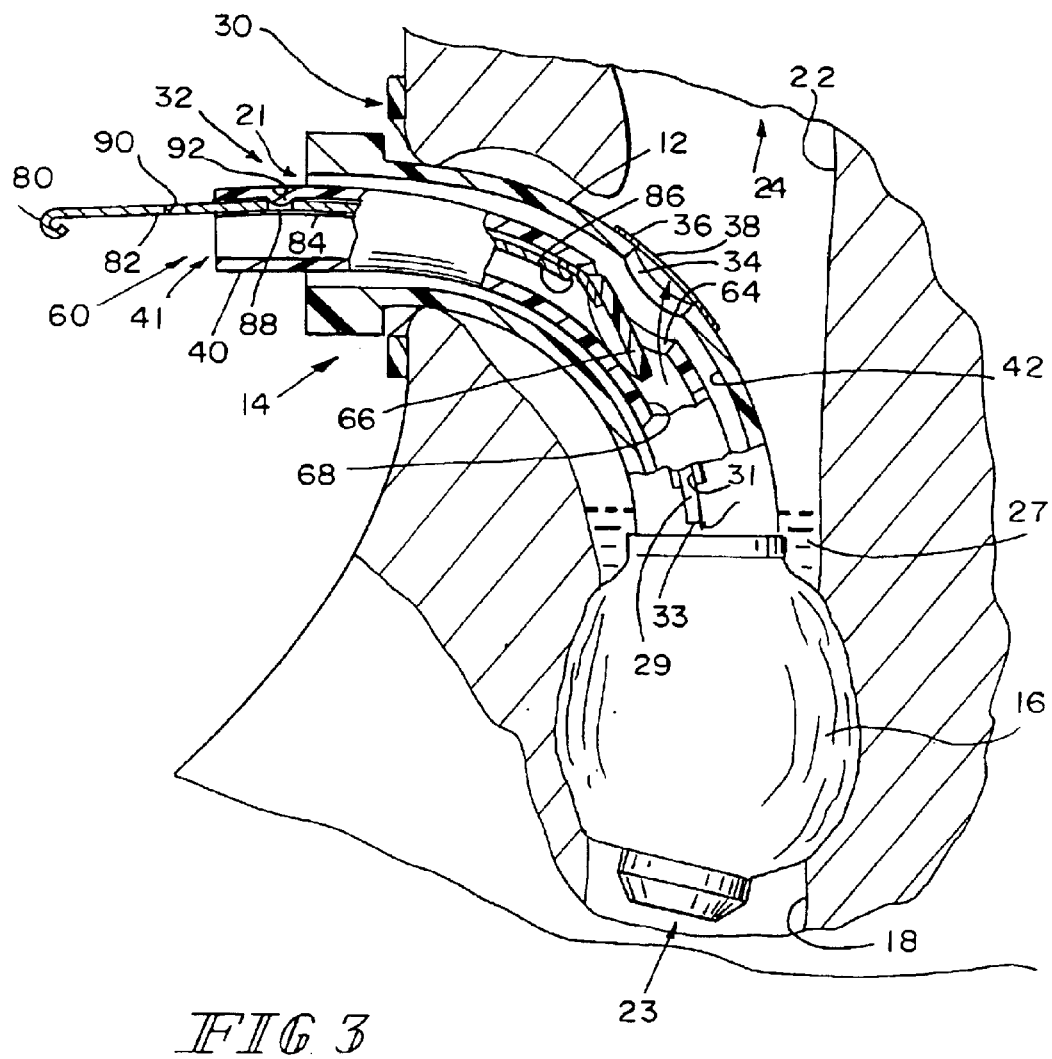
FIG. 3 illustrates a somewhat enlarged, partly fragmentary lateral section through the trachea, tracheostoma and lower pharynx of a wearer fitted with a device according to the present invention, with the device illustrated in the position it assumes during exhalation by the wearer.
Figure 5:
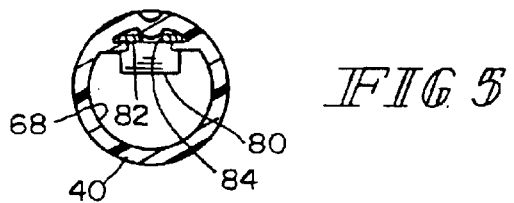
FIG. 5 illustrates a fragmentary sectional view through the embodiment illustrated in FIGS. 1–4, taken generally along section lines 5—5 of FIG. 4.
Figure 4:
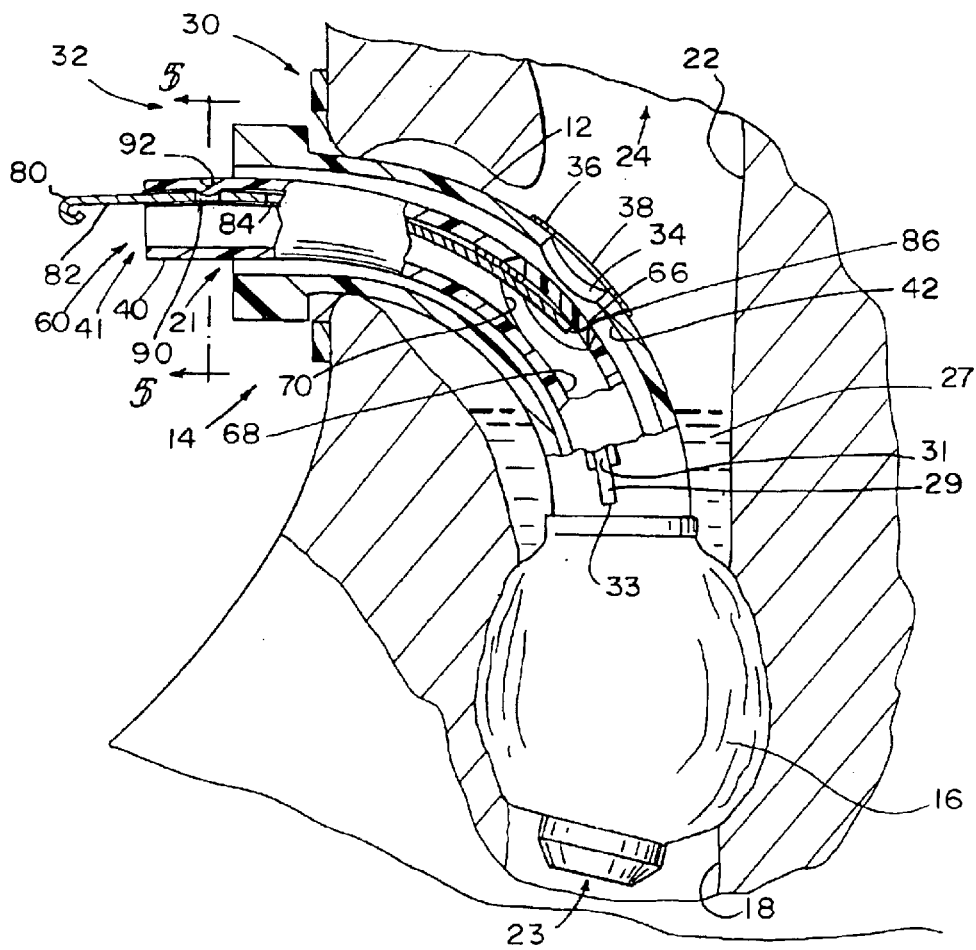
FIG. 4 illustrates a somewhat enlarged, partly fragmentary lateral section through the trachea, tracheostoma and lower pharynx of a wearer fitted with the device of FIG. 3 illustrated in another position.

Referring now to FIGS. 1–5, a speaking tracheotomy tube system 10 includes an outer cannula 12 for insertion into a tracheostoma 14. Outer cannula 12 includes an inflatable cuff 16. Cuff 16 lies in the trachea 18 of the wearer 20 below the passageway 22 upward into the pharynx 24 of the wearer 20. Outer cannula 12 also includes a first port 21 which resides outside the neck of the wearer 20 during use and a second port 23 which resides inside the neck of the wearer 20 below cuff 16 during use. The cuff 16 is inflatable through a line 26 (illustrated only in FIG. 1, for the purpose of clarity) once the outer cannula 12 is in place in the trachea 18 to prevent the passage of secretions 27 from the upper respiratory tract, including pharynx 24, downward into the lungs of the wearer 20. Such secretions inevitably pool 27 above the cuff 16 when the cuff 16 is inflated in place. To evacuate such pooling secretions 27, a tube 29 extends in an indentation 31 provided therefor down the outer sidewall of outer cannula 12. Tube 29 terminates at an open end 33 just above the level of the cuff 16. The pooled secretions 27 are evacuated by the application of a vacuum 37 (illustrated only in FIG. 2, for the purpose of clarity) to the outer end 35 of tube 29.

The outer cannula 12 includes a pivotally mounted attachment plate 30 adjacent its proximal end 32 to facilitate attachment, for example, by a strap or belt around the neck of the wearer 20. The outer cannula 12 also includes a fenestration 34 which permits the wearer 20 to speak by forcing exhaled gases upward through the fenestration 34 and into the pharynx 24. Speech may then be articulated in accordance with known principles. Although only one such fenestration 34 is illustrated, it should be understood that any number of fenestrations 34 may be provided in the outer cannula 12 for this purpose. The fenestration 34 is covered by a flexible sheet 36 of, for example, a suitable elastomer, which contains a slit 38 for the passage of exhaled gases upward through the pharynx 24. The flexible sheet 36 is provided to prevent the growth of so-called granulation tissue from the trachea 18 into the outer cannula 12 in accordance with known principles. While this covering 36 for the fenestration 34 is the only one illustrated in the drawings, numerous techniques for covering the fenestration 34 are known. See, for example, U.S. Ser. No. 09/360,274 and U.S. Ser. No. 08/996,282.

The speaking tracheotomy tube system 10 also includes an inner cannula 40 which is insertable through the lumen 42 of the outer cannula 12. Inner cannula 40 includes a port 41 at an end thereof which lies adjacent port 21 when inner cannula 40 is inserted into its use orientation within outer cannula 12 and a port 43 which lies adjacent port 23 when inner cannula 40 is inserted into its use orientation within outer cannula 12. Inner cannula 40 also includes a connector 60 portion for connecting the inner cannula 40 to a ventilator 62, illustrated in block form only in FIG. 2, for the purpose of clarity, to inflate the wearer's lungs.

The inner cannula 40 also includes an opening 64 and a cooperating flap 66 adjacent the fenestration 34 of the outer cannula 12. On pressurization of the inner cannula 40, the flap 66 assumes the position illustrated in FIG. 4 in which air from the ventilator 62 passes freely down the lumen 68 of the inner cannula 40 into the lungs of the wearer 20. The escape of air upward when the flap 66 is in this position is prevented by the cuff 16 and by the orientation of flap 66 illustrated in FIG. 4 in which flap 66 seals opening 64. However, the inner cannula 40, including its flap 66, is constructed so that, on depressurization of the ventilator 62, the flap 66 moves to the position illustrated in FIG. 3, directing the exhaled air upward out of the inner cannula 40, through the fenestration 34 with its slitted flexible sheet 36, and upward into the pharynx 24 of the wearer 20 for use in producing speech. A seat 70 for the flap 66 is provided inside inner cannula 40 when the flap 66 is in its position illustrated in FIG. 3 to reduce the likelihood of the escape of exhaled gases back through the ventilator connector 60.

The flap 66 can have a plan view somewhat the shape of a ping pong paddle, with the sealing portion of the flap 66 corresponding to the hitting portion of the paddle and the hinge portion of the flap 66 corresponding to the handle of the paddle. In order to reduce the likelihood of eversion of the flap 66 through its seat 70, the flap 66 can be constructed from a stiffer material, such as, for example, a stiffer silicone, or may be molded with a reinforcement to stiffen it, such as, for example, a molded-in X-shaped wire reinforcement or an X-shaped boss on one or the other or both of its major surfaces, or the like. The hinge, or handle of the ping pong paddle, can, for example, be located in a notch provided therefor in the wall of the cannula 40 where it is attached by an appropriate adhesive, or can be inserted into an opening provided therefor in the wall of the cannula 40 where it is attached by an appropriate adhesive, or can be attached to the inner surface of the wall of the cannula 40 by an appropriate adhesive.

Typically, ventilators 62 are provided with mechanisms to measure exhaled gas volume and alarms to indicate when recovered gas volume during exhalation is much less than output gas volume during the pressurization phase of the ventilator 62s' operation. These mechanisms, or at least the alarms of these mechanisms, may have to be disconnected to prevent the alarms from sounding during use of the inner cannula 40 by the wearer 20 during speaking sessions.

The tracheotomy tube system 10 can be quickly converted into a conventional tracheotomy tube by pushing the formed proximal end 80 of a somewhat blade-shaped lock 82 inward. See FIG. 4. Lock 82 is slidable in a channel 84 provided therefor within lumen 68. See FIG. 5. The distal end 86 of lock 82 lies adjacent the inside surface of flap 66. When lock 82 is slid distally in channel 84, its distal end 86 interferes with the opening of flap 66 to its orientation illustrated in FIG. 3. See FIG. 4. This prevents the escape of air upward through opening 64, but provides relatively unrestricted access through lumen 68 to the wearer 20's trachea 18. Alternatively, the tracheotomy tube system 10 can be converted into a conventional tracheotomy tube by removing inner cannula 40 and inserting a non-fenestrated, non-valved conventional inner cannula (not shown) into lumen 42. To provide positive positioning of blade 82 in one or the other of its non-speaking (FIG. 4) or speaking (FIG. 3) orientations, blade 82 is provided with two holes 88, 90 adjacent its proximal end 80. A nub 92 is provided on the inside wall of cannula 40 adjacent its proximal end. When blade 82 is in its speaking orientation (FIG. 3), nub 92 engages in hole 88. When blade 82 is in its non-speaking orientation (FIG. 4), nub 92 engages in hole 90.

Figure 6:
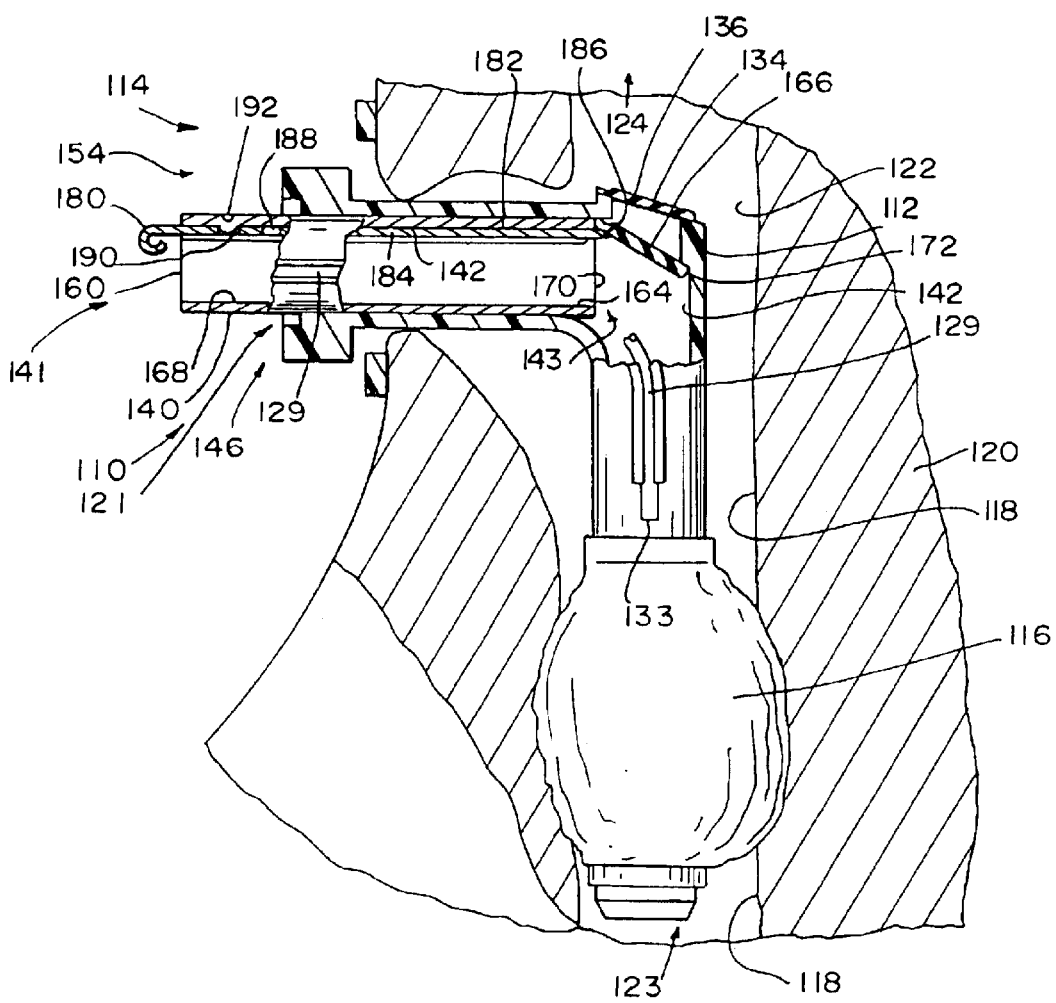
FIG. 6 illustrates a partly fragmentary lateral section through the trachea, tracheostoma and lower pharynx of a wearer fitted with another device according to the present invention in the position it assumes during exhalation by the wearer.
Figure 7:
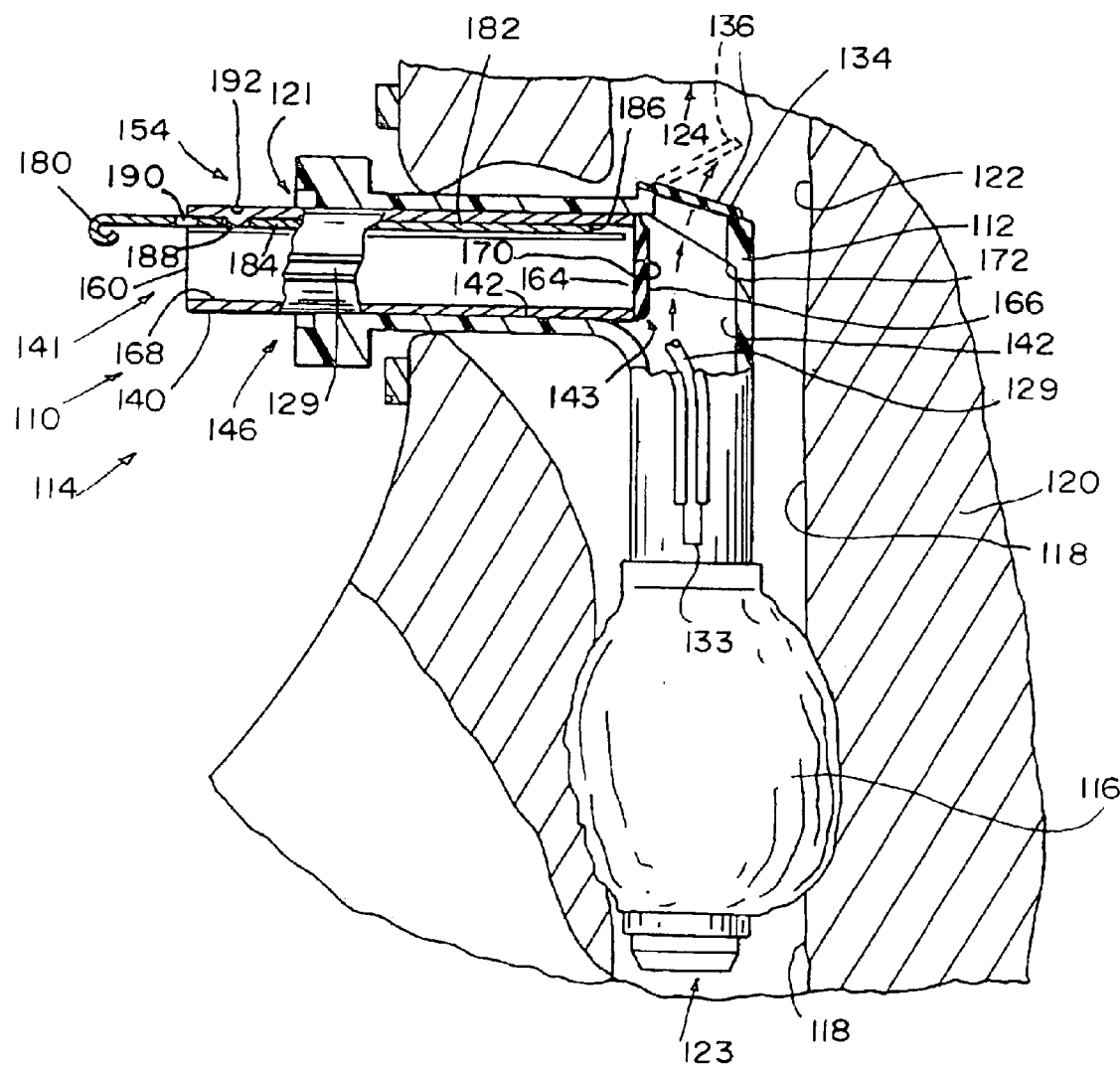
FIG. 7 illustrates a partly fragmentary lateral section through the trachea, tracheostoma and lower pharynx of a wearer fitted with the device illustrated in FIG. 6, with the device illustrated in another position it assumes.

In another embodiment of the invention illustrated in FIGS. 6–7, a speaking tracheotomy tube system 110 includes an outer cannula 112 for insertion into a tracheostoma 114. Outer cannula 112 includes an inflatable cuff 116. Cuff 116 lies in the trachea 118 of the wearer 120 below the passageway 122 upward into the pharynx 124 of the wearer 120. Outer cannula 112 also includes a first port 121 which resides outside the neck of the wearer 120 during use and a second port 123 which resides inside the neck of the wearer 120 below cuff 116 during use. The cuff 116 is inflatable through a line (not shown) once the outer cannula 112 is in place in the trachea 118 to prevent the passage of secretions from the upper respiratory tract, including pharynx 124, downward into the lungs of the wearer 120. A tube 129 extends in an indentation 131 provided therefor down the outer sidewall of outer cannula 112. Tube 129 terminates at an open end 133 just above the level of the cuff 116. Pooled secretions are evacuated by the application of a vacuum to the outer end (not shown) of tube 129.

The outer cannula 112 includes a fenestration 134 which permits the wearer 120 to speak by forcing exhaled gases upward through the fenestration 134 and into the pharynx 124. Speech may then be articulated in accordance with known principles. The fenestration 134 is covered by a flexible flap 136 of, for example, a suitable elastomer, which moves upward to the position illustrated in broken lines in FIG. 7 for the passage of exhaled gases upward through the pharynx 124. Again, the flap 136 is provided to prevent the growth of granulation tissue from the trachea 118 into the outer cannula 112. See, for example, U.S. Ser. No. 09/360, 274 and U.S. Ser. No. 08/996,282.

The speaking tracheotomy tube system 110 also includes an inner cannula 140 which is insertable through the lumen 142 of the outer cannula 112. Inner cannula 140 includes a port 141 at an end thereof which lies adjacent port 121 when inner cannula 140 is inserted into its use orientation within outer cannula 112 and a port 143 which lies adjacent port 123 when inner cannula 140 is inserted into outer cannula 112. Inner cannula 140 also includes a connector 160 for connecting the inner cannula 140 to a ventilator 162, illustrated in block form in FIG. 6 only, for the purpose of clarity, to inflate the wearer's lungs.

The inner cannula 140 also includes an opening 164 and a cooperating flap 166 adjacent the fenestration 134 of the outer cannula 112. On pressurization of the inner cannula 140, the flap 166 swings upward to the position illustrated in FIG. 6 in which air from the ventilator 162 passes freely through the lumens 142, 168 of the outer and inner cannulae 112, 140, respectively, into the lungs of the wearer 120. The escape of air upward when the flap 166 is in this position is prevented by the cuff 116 and by the orientation of flap 166 illustrated in FIG. 6 in which flap 166 seals against the seat 172. However, the inner cannula 140, including its flap 166, is constructed so that, on depressurization of the ventilator 162, the flap 166 swings downward to the position illustrated in FIG. 7, directing the exhaled air upward out of the inner cannula 140, through the fenestration 134 with its flexible flap 136, and upward into the pharynx 124 of the wearer 120 for use in producing speech. Seats 170, 172 are provided for the flap 166 at the distal end of the inner cannula 140 and inside fenestration 134, respectively, for when the flap 166 is in its positions illustrated in FIGS. 7 and 6, respectively. Seat 170 reduces the likelihood of the escape of exhaled gases back through the ventilator connector 160. Orientation markers (not shown) may be provided on the proximal end 154 of the outer cannula 112 and the proximal end 146 of the inner cannula 140 to permit the proper orientation of flap 166 with respect to seat 170.

Again, the flap 166 has somewhat the shape of a ping pong paddle in elevation, with the sealing portion of the flap 166 corresponding to the hitting portion of the paddle and the hinge portion of the flap 166 corresponding to the handle of the paddle. In order to reduce the likelihood of eversion of the flap 166 through its opening 164, the flap 166 can be constructed from a stiffer material, such as, for example, a stiffer silicone, or may be molded with a reinforcement to stiffen it, such as, for example, a molded-in X-shaped wire reinforcement or an X-shaped boss on one or the other or both of its major surfaces, or the like. Again, the hinge, or handle of the ping pong paddle, can be located in a notch provided therefor in the wall of the cannula 40 where it is attached by an appropriate adhesive, or inserted into an opening provided therefor in the wall of the cannula 140 where it is attached by an appropriate adhesive, or attached to the inner surface of the wall of the cannula 140 by an appropriate adhesive.

The tracheotomy tube system 110 can be quickly converted into a conventional tracheotomy tube by pushing the formed proximal end 180 of a somewhat blade-shaped lock 182 inward. See FIG. 6. Lock 182 is slidable in a channel 184 provided therefor within lumen 168. The distal end 186 of lock 182 lies adjacent the front surface of flap 166. When lock 182 is slid distally in channel 184, its distal end 186 interferes with the opening of flap 166 to its orientation illustrated in FIG. 7. See FIG. 6. This prevents the escape of air upward through opening 164, but provides relatively unrestricted access through lumen 168 to the wearer 120's trachea 118. Alternatively, the tracheotomy tube system 110 can be converted into a conventional tracheotomy tube by removing inner cannula 140 and inserting a non-fenestrated, non-valved conventional inner cannula (not shown) into lumen 142. To provide positive positioning of blade 182 in one or the other of its non-speaking (FIG. 6) or speaking (FIG. 7) orientations, blade 182 is provided with two holes 188, 190 adjacent its proximal end 180. A nub 192 is provided on the inside wall of cannula 140 adjacent its proximal end. When blade 182 is in its speaking orientation (FIG. 7), nub 192 engages in hole 188. When blade 182 is in its non-speaking orientation (FIG. 6), nub 192 engages in hole 190.

Figure 8:
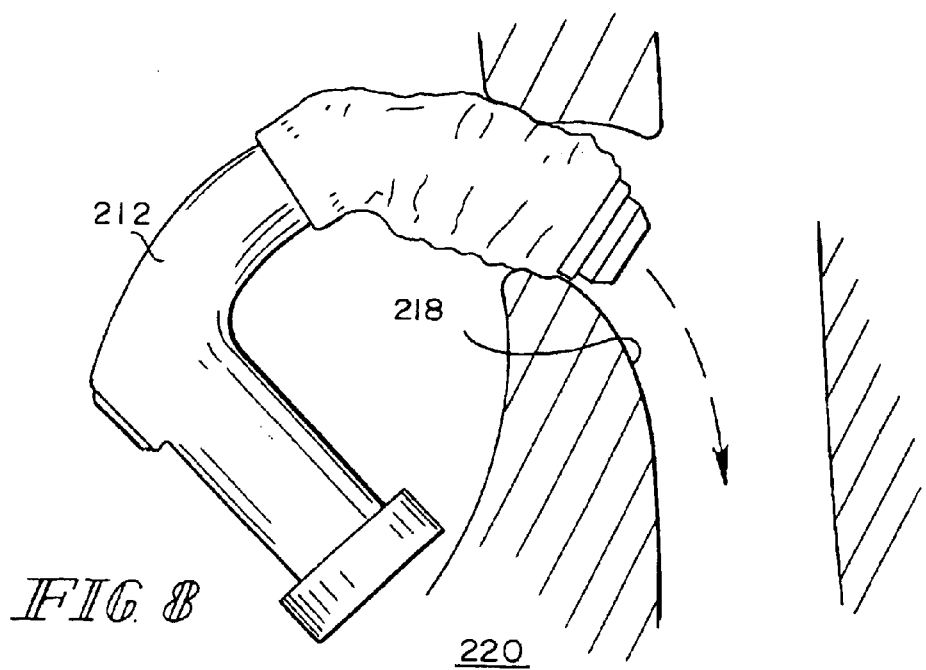
FIG. 8 illustrates a partly fragmentary lateral section through the trachea, tracheostoma and lower pharynx of a wearer fitted with another device according to the present invention, with the device illustrated in its orientation during insertion into the trachea of the wearer.
Figure 9:
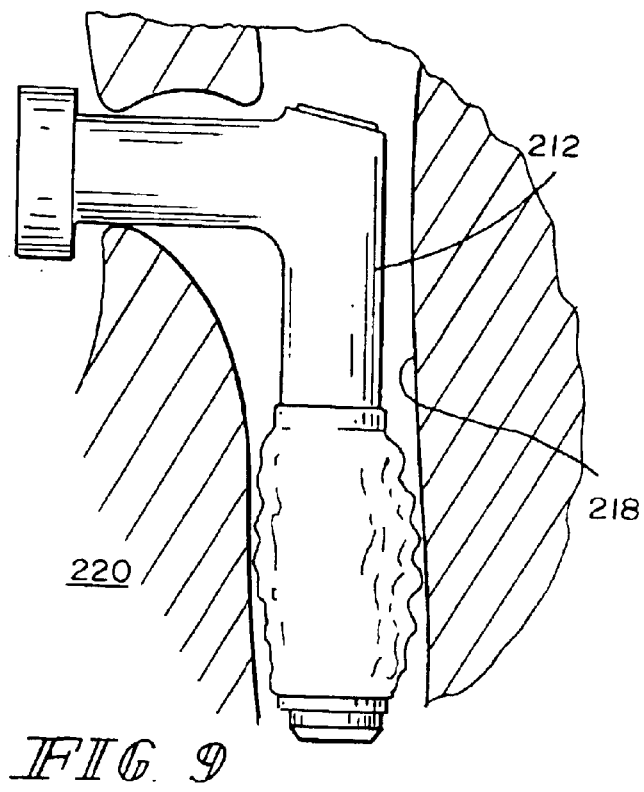
FIG. 9 illustrates a partly fragmentary lateral section through the trachea, tracheostoma and lower pharynx of a wearer fitted with the device illustrated in FIG. 8, with the device illustrated in the orientation it assumes once it has been inserted into the trachea of the wearer and warmed substantially to body temperature.

The embodiments of FIGS. 1–5 and 5–6 illustrate two different configurations of outer cannulae. While the configuration illustrated in FIGS. 1–5 is easier to insert into, and remove from, the trachea of a wearer, the configuration illustrated in FIGS. 6–7 has a more natural shape. That is, the configuration of the trachea and tracheostoma of a wearer is configured rather more like the inverted L configuration of outer cannula 112 and inner cannula 140 and rather less like the curved configuration of outer cannula 12 and inner cannula 40. According to another aspect of the invention, an outer cannula 212 is provided which is constructed from a thermoplastic resin which has the somewhat more curved configuration of outer cannula 12 when outer cannula 212 is at temperatures somewhat lower than body temperature, illustrated in FIG. 8, but which reverts to the somewhat more inverted L configuration of outer cannula 112 when it is inserted into the trachea of a wearer. See FIG. 9. This characteristic facilitates insertion of the outer cannula 212 into the trachea 218 of a wearer 220, while providing the somewhat more natural inverted L configuration once the outer cannula 212 is inserted. Of course, removal is rendered somewhat more difficult, but such outer cannulae 212 typically reside for extended times in their wearers 220.

Figure 11:
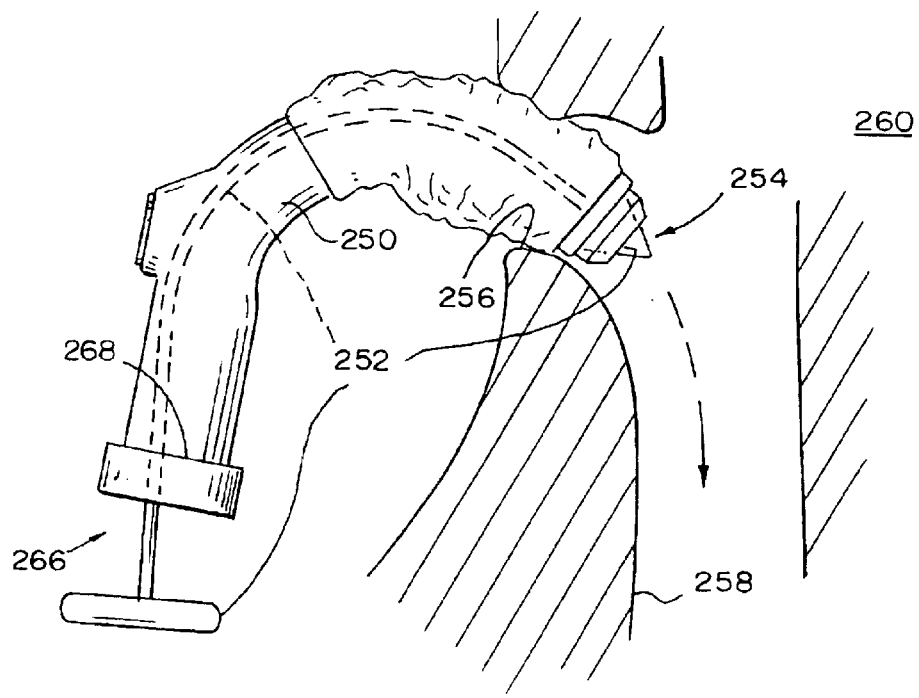
Figure 10:
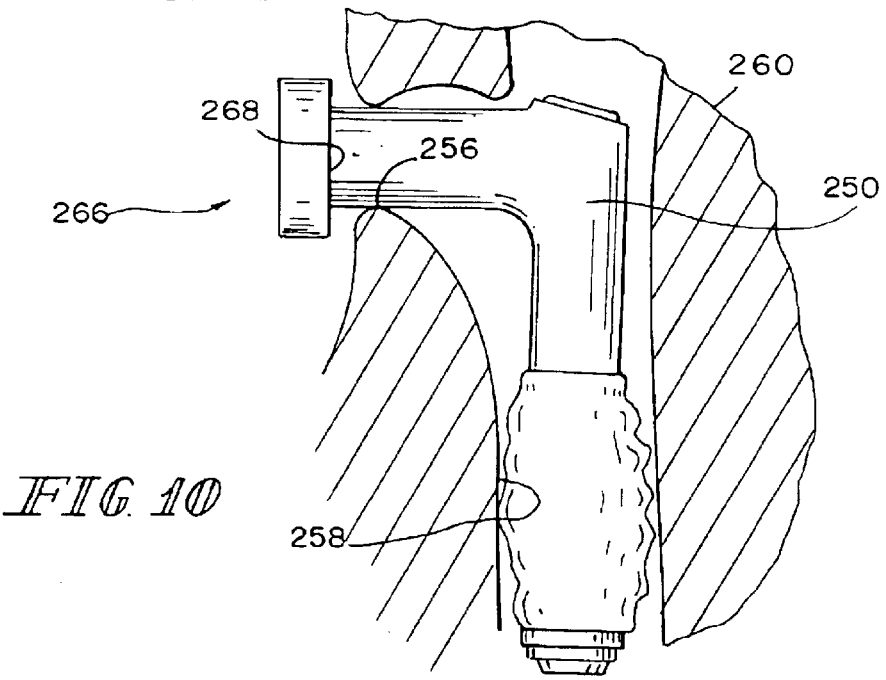
FIG. 10 illustrates a partly fragmentary lateral section through the trachea, tracheostoma and lower pharynx of a wearer fitted with another device constructed according to the invention, with the device illustrated in a use orientation; and, FIG. 11 illustrates a partly fragmentary lateral section through the trachea, tracheostoma and lower pharynx of a wearer fitted with the device illustrated in FIG. 10, with the device illustrated in an insertion orientation.

In another embodiment constructed according to the invention and illustrated in FIGS. 10–11, a relatively pliable, for example, relatively low-durometer silicone, tracheotomy tube 250 of a somewhat L-shaped configuration is provided with a stylet 252 having a somewhat bullet-shaped remote end 254 for ease of insertion through a tracheostoma 256 into the trachea 258 of a wearer 260. The proximal end 266 of the tracheotomy tube 250 is provided with some means such as, for example, a flange 268, to permit the healthcare worker to hold the proximal end 266 of the tracheotomy tube 250 so that the stylet 252 can be inserted into the open proximal end 266 of the tube 250 and pushed the full length into the tracheotomy tube 250 to cause deflection of the relatively pliable tracheotomy tube 250 from its somewhat L-shaped configuration illustrated in FIG. 10 into a somewhat more curved configuration illustrated in FIG. 11. This configuration facilitates insertion of the tracheotomy tube 250 through the tracheostoma 256 and into the trachea 258 of the wearer 260. Once the tracheotomy tube 250 is in place in the trachea 258 of the wearer 260, the stylet 252 is removed, at which time the tracheotomy tube 250 returns from its somewhat more curved configuration illustrated in FIG. 11 to its somewhat more L-shaped configuration illustrated in FIG. 10.

To remove the tracheotomy tube 250 from the trachea 258 of the wearer 260, the stylet 252 can be reinserted into the tracheotomy tube 250 to return it to its somewhat more curved configuration illustrated in FIG. 11 prior to removing it from the trachea 258 of the wearer 260. If this is done, the tracheotomy tube 250 comes out relatively easily. Alternatively, the tracheotomy tube 250 can be removed while still in its somewhat more L-shaped configuration. Although this requires somewhat more force than if the stylet 252 were used to render the tracheostomy tube 250 somewhat more curved in configuration, the tracheotomy tube 250 still can be removed without excessive effort or damage to the trachea 258 or tracheostoma 256 of the wearer 260. The tracheotomy tube 250 is otherwise configured similarly to tracheotomy tube 112, 140 illustrated in FIGS. 6–7.

While many details of the embodiments illustrated in FIGS. 1–7 are eliminated from the illustrations of FIGS. 8–11 for the purpose of clarity, it is to be understood that practical embodiments of the invention illustrated in FIGS. 8–11 can be provided with, for example, secretion evacuation tubes like tubes 29, 129 illustrated in FIGS. 1–7.

What is claimed is:

1. In combination, an outer cannula having a first port for orienting outside the neck of a wearer, a second port for orienting within the trachea of the wearer and a first passageway coupling the first port to the second port to permit the flow of gases from the first port to the second during inhalation by the wearer and from the second port during exhalation by the wearer, a third port between the first and second ports, and an inner cannula for insertion into the first passageway via the first port when the wearer desires to be able to exhale through the wearer's pharynx, the inner cannula including a fourth port for orienting adjacent the first port, a fifth port for orienting adjacent the second port and a second passageway coupling the fourth port to the fifth port to permit the flow of gases from the fourth port to the fifth during inhalation by the wearer and from the fifth port during exhalation by the wearer, a valve controlling flow through the third port, the valve assuming a first orientation to permit flow from the first port to the second port when the first port is at a higher pressure than the second port, and a second orientation to permit flow from the second port through the third port when the second port is at a higher pressure than the first port.

2. The apparatus of claim 1 wherein the valve includes a movable member and a seat, the movable member moving away from the seat to permit flow from the fourth port to the fifth port when the fourth port is at a higher pressure than the fifth port, and seating against the seat to impede flow from the fifth port through the fourth port and promote flow from the fifth port through the third port when the fourth port is at a lower pressure than the fifth port.

3. The apparatus of claim 2 wherein the seat is provided in the second passageway.

4. The apparatus of claim 3 including a second seat, the movable member moving toward the second seat to impede flow from the fourth port through the third port when the fourth port is at a higher pressure than the fifth port, and moving away from the second seat to permit flow from the fifth port through the third port when the fourth port is at a lower pressure than the fifth port.

5. The apparatus of claim 4 wherein the outer cannula includes an inflatable cuff between the second and third ports and a third passageway for introducing an inflating fluid into the cuff in situ in the trachea of the wearer to impede the flow of fluids between the cuff and the trachea when the cuff is inflated.

6. The apparatus of claim 3 wherein the outer cannula includes an inflatable cuff between the second and third ports and a third passageway for introducing an inflating fluid into the cuff in situ in the trachea of the wearer to impede the flow of fluids between the cuff and the trachea when the cuff is inflated.

7. The apparatus of claim 2 wherein the seat is provided in the first passageway.

8. The apparatus of claim 4 including a second seat, the movable member moving toward the second seat to impede flow from the fourth port through the third port when the fourth port is at a higher pressure than the fifth port, and moving away from the second seat to permit flow from the fifth port through the third port when the fourth port is at a lower pressure than the fifth port.

9. The apparatus of claim 8 wherein the outer cannula includes an inflatable cuff between the second and third ports and a third passageway for introducing an inflating fluid into the cuff in situ in the trachea of the wearer to impede the flow of fluids between the cuff and the trachea when the cuff is inflated.

10. The apparatus of claim 7 wherein the outer cannula includes an inflatable cuff between the second and third ports and a third passageway for introducing an inflating fluid into the cuff in situ in the trachea of the wearer to impede the flow of fluids between the cuff and the trachea when the cuff is inflated.

11. The apparatus of claim 2 including a second seat, the movable member moving toward the second seat to impede flow from the fourth port through the third port when the fourth port is at a higher pressure than the fifth port, and moving away from the second seat to permit flow from the fifth port through the third port when the fourth port is at a lower pressure than the fifth port.

12. The apparatus of claim 11 wherein the outer cannula includes an inflatable cuff between the second and third ports and a third passageway for introducing an inflating fluid into the cuff in situ in the trachea of the wearer to impede the flow of fluids between the cuff and the trachea when the cuff is inflated.

13. The apparatus of claim 2 wherein the outer cannula includes an inflatable cuff between the second and third ports and a third passageway for introducing an inflating fluid into the cuff in situ in the trachea of the wearer to impede the flow of fluids between the cuff and the trachea when the cuff is inflated.

14. The apparatus of claim 1 wherein the valve includes a movable member and a seat, the movable member moving toward the seat to impede flow from the fourth port through the third port when the fourth port is at a higher pressure than the fifth port, and moving away from the seat to permit flow from the fifth port through the third port when the fourth port is at a lower pressure than the fifth port.

15. The apparatus of claim 14 wherein the outer cannula includes an inflatable cuff between the second and third ports and a third passageway for introducing an inflating fluid into the cuff in situ in the trachea of the wearer to impede the flow of fluids between the cuff and the trachea when the cuff is inflated.

16. The apparatus of claim 1 wherein the outer cannula includes an inflatable cuff between the second and third ports and a third passageway for introducing an inflating fluid into the cuff in situ in the trachea of the wearer to impede the flow of fluids between the cuff and the trachea when the cuff is inflated.

17. The apparatus of claim 1, 2, 3, 4, 5, 6, 7, 8, 9, 10, 11, 12, 13, 14, 15 or 16 wherein the outer cannula includes a flexible member for covering the third port.

18. The apparatus of claim 17 wherein the flexible member and the outer cannula including complementary first and second attachment members, respectively, for attaching the flexible member to the outer cannula, the second attachment member providing an attachment point located within the third port for attachment of the first attachment member to the second attachment member at the attachment point.

19. The apparatus of claim 17 wherein the flexible member comprises a flexible membrane having a slit in it.

20. The apparatus of claim 17 wherein the flexible member comprises a flap for covering the third port.

21. The apparatus of claim 1, 2, 3, 4, 5, 6, 7, 8, 9, 10, 11, 12, 13, 14, 15 or 16 further including a member selectively movable into interfering relationship to the valve, the member preventing the valve from moving to the second orientation.

22. A tracheotomy cannula having a first port for orienting outside the neck of a wearer, a second port for orienting within the trachea of the wearer and a first passageway between the first port and the second port to permit the flow of gases from the first port to the second during inhalation by the wearer and from the second port during exhalation by the wearer, the cannula including a portion formed from a thermoplastic material having a first, generally curved orientation when said portion is maintained substantially below body temperature and a second, somewhat inverted L-shaped configuration when said portion is warmed substantially to body temperature.

23. A tracheotomy cannula having a first port for orienting outside the neck of a wearer, a second port for orienting within the trachea of the wearer and a first passageway between the first port and the second port to permit the flow of gases from the first port to the second during inhalation by the wearer and from the second port during exhalation by the wearer, the cannula including a portion formed from a first material, and a stylet formed from a second material, the first material being more flexible than the second, the stylet having a generally curved orientation, the tracheotomy cannula having a somewhat inverted L-shaped configuration when the stylet is not inserted into the first passageway and a generally curved orientation when the stylet is inserted into the first passageway.

* * * * *